US007601731B2

(12) United States Patent
Raad

(10) Patent No.: US 7,601,731 B2
(45) Date of Patent: Oct. 13, 2009

(54) ANTIMICROBIAL FLUSH SOLUTIONS

(75) Inventor: Issam Raad, Missouri City, TX (US)

(73) Assignee: Board of Regents, the University of Texas System, Austin, TX (US)

( * ) Notice: Subject to any disclaimer, the term of this patent is extended or adjusted under 35 U.S.C. 154(b) by 0 days.

(21) Appl. No.: 10/862,830

(22) Filed: Jun. 7, 2004

(65) Prior Publication Data

US 2005/0013836 A1  Jan. 20, 2005

Related U.S. Application Data

(60) Provisional application No. 60/476,555, filed on Jun. 6, 2003.

(51) Int. Cl.
*A01N 43/48* (2006.01)
(52) U.S. Cl. .................................................. 514/279
(58) Field of Classification Search ....................... None
See application file for complete search history.

(56) References Cited

U.S. PATENT DOCUMENTS

| 4,213,979 | A | * | 7/1980 | Levine ........................ 514/171 |
| 4,233,263 | A | | 11/1980 | Schaeffer ..................... 422/28 |
| 4,349,029 | A | | 9/1982 | Mott ........................ 128/349 B |
| 4,592,920 | A | | 6/1986 | Murtfeldt ....................... 427/2 |
| 4,863,445 | A | | 9/1989 | Mayhan et al. ............. 604/317 |
| 5,286,479 | A | * | 2/1994 | Garlich et al. ................ 424/54 |
| 5,310,524 | A | | 5/1994 | Campbell et al. ............. 422/33 |
| 5,344,652 | A | | 9/1994 | Hall, II et al. ............... 424/405 |
| 5,362,754 | A | | 11/1994 | Raad et al. ................... 514/566 |
| 5,589,507 | A | | 12/1996 | Hall, II et al. ............... 514/557 |
| 5,688,516 | A | | 11/1997 | Raad et al. .................. 424/409 |
| 5,820,607 | A | | 10/1998 | Tcholakain et al. ......... 604/265 |
| 5,840,343 | A | | 11/1998 | Hall, II et al. ............... 424/616 |
| 5,871,692 | A | | 2/1999 | Haire et al. ................... 422/28 |
| 5,872,104 | A | * | 2/1999 | Vermeulen et al. ............ 514/29 |
| 5,891,422 | A | * | 4/1999 | Pan et al. ..................... 424/49 |
| 6,068,972 | A | | 5/2000 | Levy .............................. 435/4 |
| 6,150,405 | A | * | 11/2000 | Proctor ....................... 514/474 |
| 6,165,484 | A | | 12/2000 | Raad et al. .................. 424/405 |
| 6,187,768 | B1 | | 2/2001 | Wele et al. .................. 514/199 |
| 6,261,457 | B1 | | 7/2001 | Wenthold et al. ........... 210/636 |
| 6,267,979 | B1 | | 7/2001 | Raad et al. .................. 424/405 |
| 6,350,251 | B1 | | 2/2002 | Prosl et al. .................. 604/93 |
| 6,361,524 | B1 | | 3/2002 | Odell et al. ................. 604/187 |
| 6,368,317 | B2 | | 4/2002 | Chang ......................... 604/544 |
| 6,428,799 | B1 | | 8/2002 | Cen et al. .................... 424/402 |
| 6,448,006 | B1 | | 9/2002 | Levy ............................. 435/6 |
| 6,503,539 | B2 | | 1/2003 | Gestrelius et al. ........... 424/549 |
| 6,509,319 | B1 | | 1/2003 | Raad et al. ................... 514/31 |
| 6,559,116 | B1 | * | 5/2003 | Godfroid et al. ............ 510/499 |
| 6,585,934 | B1 | | 7/2003 | Oberleitner et al. ........... 422/28 |
| 6,592,564 | B2 | | 7/2003 | Finch et al. ................. 604/500 |
| 6,679,870 | B1 | | 1/2004 | Finch et al. ................. 604/500 |
| 6,685,694 | B2 | | 2/2004 | Finch et al. ................. 604/508 |
| 2002/0007175 | A1 | | 1/2002 | Chang ......................... 604/544 |
| 2002/0010438 | A1 | * | 1/2002 | Finch et al. ................. 604/265 |
| 2002/0052404 | A1 | | 5/2002 | Hunter et al. ................ 514/449 |
| 2002/0087156 | A1 | | 7/2002 | Maguire et al. ............... 606/41 |
| 2002/0133072 | A1 | | 9/2002 | Wang et al. ................. 600/423 |
| 2003/0007939 | A1 | | 1/2003 | Murad .......................... 424/61 |
| 2003/0032605 | A1 | | 2/2003 | Raad et al. .................... 514/28 |
| 2003/0065292 | A1 | | 4/2003 | Darouiche et al. .......... 604/265 |
| 2003/0099718 | A1 | * | 5/2003 | Burrell et al. ............... 424/618 |

FOREIGN PATENT DOCUMENTS

| EP | 0285382 | 4/1987 |
| EP | 0348947 | 1/1990 |
| EP | 1245247 | 10/2002 |
| WO | WO 94/10838 | 5/1994 |
| WO | WO 95/05203 | 2/1995 |
| WO | WO 95/32625 | 12/1995 |
| WO | WO 9713495 A1 * | 4/1997 |
| WO | WO 97/18707 | 5/1997 |
| WO | WO 9730685 A1 * | 8/1997 |
| WO | WO 99/17791 | 4/1999 |
| WO | WO 00/01238 | 1/2000 |
| WO | WO 00/07574 | 2/2000 |
| WO | WO 01/54661 | 8/2001 |
| WO | WO 02/45611 | 6/2002 |

OTHER PUBLICATIONS

S.L. Werlin, et al. J. Parent. Enteral Nutr. (1995) 19(5), pp. 416-418.*
A. Aydemir "Why 70% EtOH for cleaning?" internet document <http://www.bio.net/bionet/mm/methods/1995-June/029902.html> Jun. 19, 1995, 2 pages; accessed Aug. 25, 2006.*
D.A. Johnson et al. Clin. Nutr. (1992) 11(2), pp. 97-100.*
I. Raad et al. Antimicrob. Agent Chemother. (2007) 51(1), pp. 78-83.*
G. McDonnell and D. Russell. Clin. Microbiol. Rev. (1999) 12(1) pp. 147-179.*
L.W. Bush et al. J. Clin. Microbiol. (1986) 24(3), pp. 343-348.*
C.H. Sissons et al. Arch. Oral Biol. (1996) 41(1), pp. 27-34.*
N. Kurita and S. Koike, Argic. Biol. Chem. (1983) 47(1), pp. 67-75.*
"Biofilm: disinfecting biofilms using hydrogen peroxide/silver based biocide," Accepta: Leading eChemical Procurement, http://accepta.com, 2004.
"Removal of residual microbicide from sterilised medical devices—using a neutralising sol. comprising, e.g. ascorbic acid or an enzyme," Dialog File, Derwent WPI, Thompson Derwent, 2004.
"The breakthrough technology behind STERRAD sterilization systems," Advanced Sterilization Products, Johnson & Johnson Company, http://www.sterrad.com.

(Continued)

*Primary Examiner*—Andrew D Kosar
(74) *Attorney, Agent, or Firm*—Fulbright & Jaworski LLP

(57) ABSTRACT

The present invention provides antimicrobial solutions that comprise at least one alcohol, at least one antimicrobial agent and at least one chelator and/or anticoagulant. Also provided are methods for rapidly reducing a microbe or a virus from surfaces including surfaces of indwelling medical devices and organic surfaces such as skin and sutures, and inorganic surfaces such as hospital equipment, pipelines etc.

11 Claims, 1 Drawing Sheet

OTHER PUBLICATIONS

Chatzinikolaou et al., "Minocycline and Edta (M-EDTA) as a flush solution for implantable ports (IP) used in pediatric cancer patients," *Shea Merck Healthcare Epidemiology Search Abstracts*, 2002.

Desautels et al., "Maintenance of sterility in urinary drainage bags," *Surg. Gynecol. Obstet.*, 154(6):838-840, 1982.

Johnston et al., "Ethanol flush for the prevention of catheter occlusion," *Clinical Nutrition*, 11:97-100. 1992.

Kuhn et al., "Antifungal susceptibility of Candida biofilms: unique efficacy of amphotericin B lipid formulations and echinocandins," *Antimicrobial Agents and Chemotherapy*, 46(6):1773-1780, 2002.

Lavallee et al., "Catheter cleaning for re-use in intermittent catherization: new light on an old problem," *SCI Nurs.*, 12(1):10-12, 1995.

Leon et al., "Antiseptic chamber-containing hub reduces central venous catheter-related infection: a prospective, randomized study," *Clinical Investigations*, 31(5):1318-1324, 2003.

Ma et al., "Safety issue of re-sterilization of polyurethane electrophysiology catheters: a cytotoxicity study," *J. Biomater. Sci. Polym. Ed.*, 14(3):213-226, 2003.

Pennington et al., "Ethanol lock in the management of catheter occlusion," *Journal of Parenteral and Enteral Nutrition*, 11(5):507-508, 1987.

Samuels and Fisher, "The use of hydrogen peroxide in catheter drainage units," *AUAA J.*, 3(3):5-9, 1983.

Schaeffer et al., "Bactericidal effect of hydrogen peroxide on urinary tract pathogens," *Applied and Environmental Microbiology*, 40(2):337-340, 1980.

Schaeffer, "Hydrogen peroxide warrants careful consideration for control of catheter-associated bacteriuria," *Am J. Infect. Control*, 10(4):158-160, 1982.

Shabino et al., "Home cleaning-disinfection procedure for tracheal suction catheters," *Pediatr. Infect. Dis.*, 5(1):54-58, 1986.

Shah et al., "Antimicrobial activity of a novel catheter lock solution," *Antimicrob. Agents Chemother.*, 46(6):1674-1679, 2002.

Sheretz and Bleyer, Invention Disclosure, dated Oct. 8, 1998.

Sheretz et al., "In vitro efficacy of minocycline (M)/EDTA (MEDTA) as a catheter lock solution," *Shea Merck Healthcare Epidemiology Search Abstracts*, 2002.

Sweet et al., "Evaluation of H2O2 prophylaxis of bacteriuria in patients with long-term indwelling Foley catheters: a randomized controlled study," *Infect. Control*, 6(7):263-266, 1985.

Thompson et al., "Catheter-associated bacteriuria. Failure to reduce attack rates using periodic instillations of a disinfectant into urinary drainage systems," *JAMA*, 251(6):747-751, 1984.

Washington, "Instillation of 3% hydrogen peroxide or distilled vinegar in urethral catheter drainage bag to decrease catheter-associated bacteriuria," *Biol. Res. Nurs.*, 3(2):78-87, 2001.

Heinzel, "The phenomena of resistance to disinfectants and preservatives," In *Industrial biocides*, Payne (ed.), pp. 52, 56-58, and 64-66, 1988.

Lehmann, "Synergisms in disinfectant formulations," In *Industrial biocides*, Payne (ed.), pp. 78-79 and 89, 1988.

* cited by examiner

ANTIMICROBIAL FLUSH SOLUTIONS

The present application claims the benefit of the filing date of U.S. Provisional Patent Application Ser. No. 60/476,555, filed on Jun. 6, 2003. The entire text of the above-referenced disclosure is specifically incorporated herein by reference without disclaimer.

BACKGROUND OF THE INVENTION

1. Field of the Invention

The present invention relates generally to the fields of medicine and microbiology. More particularly, it concerns methods of reducing microbial organisms from indwelling medical devices, medical equipment and other surfaces.

2. Description of Related Art

Medical devices, such as vascular catheters, have improved the quality of medical care. However, infections resulting from the colonization of organisms embedded in biofilm are the most frequent complication associated with the use of these and other indwelling and/or prosthetic devices. In fact, infections are the most serious complications associated with indwelling central venous catheters (CVCs) (Maki et al., 1998). It is estimated that more than 200,000 catheter-related bloodstream infections (CRBSI) occur annually in the United States alone (Kluger et al., 1999). *Staphylococcus epidermidis, Staphylococcus aureus* and *Candida* species are the leading organisms causing CRBSI (Maki et al., 1998; Raad et al., 2002).

Because intralumenal colonization is the major source for the migration of organisms leading to bloodstream infections in long-term silicone catheters (Raad et al., 1993), recent guidelines by the CDC and Infectious Diseases Society of America have proposed the use of intralumenal antimicrobial lock solutions for the prevention and treatment of CRBSI (Mermel et al., 2001; Centers for Disease Control and Prevention, 2002). Most long-term CVCs are typically flushed with heparin. An antimicrobial/anticoagulant combination consisting of vancomycin/heparin with and without ciprofloxacin was shown to reduce the risk of catheter-related bacteremia caused by gram-positive organisms (Carratala et al., 1999; Henrickson et al., 2002; Schwartz et al., 1990). However, with the rise of incidences of infection by vancomycin resistant gram-positive bacteria, concerns have been raised over the use of vancomycin flush solutions and their potential for increasing the risk of vancomycin resistance (Spafford et al., 1994).

Recently the present inventor demonstrated that a flush solution comprising minocycline and EDTA (M-EDTA) is highly efficacious in preventing catheter-related colonization, bacteremia and endocarditis in rabbits (Raad et al., 2002). When compared to a heparin flush solution, M-EDTA was found to decrease the risk of catheter-related colonization and infection in hemodialysis patients as well as pediatric cancer patients (Bleyer et al., 2000; Chatzinikolaou et al., 2002). EDTA has an equivalent anticoagulant activity to heparin (Reardon et al., 1991). An anticoagulant in flush solutions is necessary to prevent the thrombotic occlusion of the catheter lumen.

Although M-EDTA has been found to be efficacious in preventing CRBSI, this solution may not be applicable given some of the limitations of the real world of clinical practice. In the animal and clinical studies, the M-EDTA lock solution was required to be exposed to the surface of the indwelling medical device, such as the lumen of catheters, for at least 4 hours. In vitro studies have also shown that M-EDTA requires at least 4 hours of dwell time to eradicate organisms that colonize the lumen of the catheter (see in particular data in U.S. Pat. No. 5,362,754, columns 11 and 12, and Tables 3, 4 and 5 as well as in U.S. Pat. No. 5,688,516, columns 15 and 16, and Tables 3, 4, and 5). Providing a four hour exposure time to reduce microbes using the M-EDTA solution is usually not possible in critically ill patients who require continuous infusion therapy, including parenteral nutrition.

Thus, there is an acute need in the art to develop compositions and methods for rapid reduction and/or eradication of microbes from indwelling medical devices without interruption of the use of the device in patients for too long a period. In addition, there is also a need for better and improved antimicrobial compositions.

SUMMARY OF THE INVENTION

The present invention overcomes these and other limitations in the art and provides compositions that reduce or eradicate microbial agents from surfaces wherein the compositions comprise at least one antimicrobial agent, at least one chelator and/or anticoagulant, and at least one alcohol. The present invention also provides methods to rapidly reduce or eradicate microbial agents from surfaces.

Therefore, provided are antimicrobial solutions comprising at least one alcohol, at least one antimicrobial agent and at least one chelator and/or anticoagulant. "Antimicrobial agents" that are comprised in the solutions of the present invention include antibacterial agents, antifungal agents, antiviral agents as well as antiseptic agents. These components are present in effective amounts to reduce microbial growth.

In some embodiments of the invention, the antimicrobial agent is an antibacterial agent. While any antibacterial agent may be used in the preparation of the instant antimicrobial solutions, some non-limiting exemplary antibacterial agent(s) include those classified as aminoglycosides, beta lactams, quinolones or fluoroquinolones, macrolides, sulfonamides, sulfamethaxozoles, tetracyclines, streptogramins, oxazolidinones (such as linezolid), clindamycins, lincomycins, rifamycins, glycopeptides, polymxins, lipopeptide antibiotics, as well as pharmacologically acceptable sodium salts, pharmacologically acceptable calcium salts, pharmacologically acceptable potassium salts, lipid formulations, derivatives and/or analogs of the above.

Each of these classes of antibacterial agents have different mechanisms of action and are represented by several antibiotics a discussion of which is presented below. However, the skilled artisan will recognize that the invention is in no way limited to the agents set forth here and that these agents are described merely as examples.

The aminoglycosides are bactericidal antibiotics that bind to the 30S ribosome and inhibit bacterial protein synthesis. They are typically active against aerobic gram-negative *bacilli* and *staphylococci*. Exemplary aminoglycosides that may be used in some specific aspects of the invention include amikacin, kanamycin, gentamicin, tobramycin, or netilmicin.

Beta lactams are a class of antibacterials that inhibit bacterial cell wall synthesis. A majority of the clinically useful beta-lactams belong to either the penicillin group (penam) or cephalosporin (cephem) groups. The beta-lactams also include the carbapenems (e.g., imipenem), and monobactams (e.g., aztreonam). Inhibitors of beta-lactamase such as clavulanic acid and its derivatives are also included in this category.

Non-limiting examples of the penicillin group of antibiotics that may be used in the solutions of the present invention include amoxicillin, ampicillin, benzathine penicillin G, carbenicillin, cloxacillin, dicloxacillin, piperacillin, or ticarcillin, etc. Examples of cephalosporins include ceftiofur, ceftiofur sodium, cefazolin, cefaclor, ceftibuten, ceftizoxime, cefoperazone, cefuroxime, cefprozil, ceftazidime, cefotaxime, cefadroxil, cephalexin, cefamandole, cefepime, cefdinir, cefriaxone, cefixime, cefpodoximeproxetil, cephapirin, cefoxitin, cefotetan etc. Other examples of beta lactams include mipenem or meropenem which are extremely active parenteral antibiotics with a spectrum against almost all gram-positive and gram-negative organisms, both aerobic and anaerobic and to which *Enterococci, B. fragilis,* and *P. aeruginosa* are particularly susceptible.

Examples of beta lactamase inhibitors include clavulanate, sulbactam, or tazobactam. In some aspects of the present invention, the antibacterial solutions may comprise a combination of at least one beta lactam and at least one beta lactamase inhibitor.

Macrolide antibiotics are another class of bacteriostatic agents that bind to the 50S subunit of ribosomes and inhibit bacterial protein synthesis. These drugs are active against aerobic and anaerobic gram-positive cocci, with the exception of enterococci, and against gram-negative anaerobes. Exemplary macrolides include erythromycin, azithromycin, clarithromycin.

Quinolones and fluoroquinolones typically function by their ability to inhibit the activity of DNA gyrase. Examples include nalidixic acid, cinoxacin, trovafloxacin, ofloxacin, levofloxacin, grepafloxacin, trovafloxacin, sparfloxacin, norfloxacin, ciprofloxacin, moxifloxacin and gatifloxacin.

Sulphonamides are synthetic bacteriostatic antibiotics with a wide spectrum against most gram-positive and many gram-negative organisms. These drugs inhibit multiplication of bacteria by acting as competitive inhibitors of p-aminobenzoic acid in the folic acid metabolism cycle. Examples include mafenide, sulfisoxazole, sulfamethoxazole, and sulfadiazine.

The tetracycline group of antibiotics include tetracycline derivatives such as tigecycline which is an investigational new drug (IND), minocycline, doxycycline or demeclocycline and analogs such as anhydrotetracycline, chlorotetracycline, or epioxytetracycline. The present inventors have previously shown that minocycline has a higher penetration of the microbial biofilm layer than vancomycin and that EDTA is unique in effectively preventing and dissolving polysaccharide-rich microbial glycocalyx (U.S. Pat. No. 5,362,754).

The streptogramin class of antibacterial agents is exemplified by quinupristin, dalfopristin or the combination of two streptogramins.

Drugs of the rifamycin class typically inhibit DNA-dependent RNA polymerase, leading to suppression of RNA synthesis and have a very broad spectrum of activity against most gram-positive and gram-negative bacteria including *Pseudomonas aeruginosa* and *Mycobacterium* species. An exemplary rifamycin is rifampicin.

Other antibacterial drugs are glycopeptides such as vancomycin, teicoplanin and derivatives thereof. Yet other antibacterial drugs are the polymyxins which are exemplified by colistin.

In addition to these several other antibacterial agents such as prestinomycin, chloramphenicol, trimethoprim, fusidic acid, metronidazole, bacitracin, spectinomycin, nitrofurantion, daptomycin or other leptopeptides, oritavancin, dalbavancin, ramoplamin, ketolide etc. may be used in preparing the compositions described herein. Of these, metronidazole is active only against protozoa, such as *Giardia lamblia, Entamoeba histolytica* and *Trichomonas vaginalis,* and strictly anaerobic bacteria. Spectinomycin, is a bacteriostatic antibiotic that binds to the 30S subunit of the ribosome, thus inhibiting bacterial protein synthesis and nitrofurantoin is used orally for the treatment or prophylaxis of UTI as it is active against *Escherichia coli, Klebsiella-Enterobacter* species, *staphylococci,* and *enterococci.*

In other embodiments, the antimicrobial agent is an antifungal agent. Some exemplary classes of antifungal agents include imidazoles or triazoles such as clotrimazole, miconazole, ketoconazole, econazole, butoconazole, omoconazole, oxiconazole, terconazole, itraconazole, fluconazole, voriconazole (UK 109,496), posaconazole, ravuconazole or flutrimazole; the polyene antifungals such as amphotericin B, liposomal amphoterecin B, natamycin, nystatin and nystatin lipid formualtions; the cell wall active cyclic lipopeptide antifungals, including the echinocandins such as caspofungin, micafungin, anidulfungin, cilofungin; LY121019; LY303366; the allylamine group of antifungals such as terbinafine. Yet other non-limiting examples of antifungal agents include naftifine, tolnaftate, mediocidin, candicidin, trichomycin, hamycin, aurefungin, ascosin, ayfattin, azacolutin, trichomycin, levorin, heptamycin, candimycin, griseofulvin, BF-796, MTCH 24, BTG-137586, pradimicins (MNS 18184), benanomicin; ambisome; nikkomycin Z; flucytosine, or perimycin.

In still other embodiments of the invention, the antimicrobial agent is an antiviral agent. Non-limiting examples of antiviral agents include cidofovir, amantadine, rimantadine, acyclovir, gancyclovir, pencyclovir, famciclovir, foscamet, ribavirin, or valcyclovir. In some embodiments the antimicrobial agent is an innate immune peptide or proteins. Some exemplary classes of innate peptides or proteins are transferrins, lactoferrins, defensins, phospholipases, lysozyme, cathelicidins, serprocidins, bacteriocidal permeability increasing proteins, amphipathic alpha helical peptides, and other synthetic antimicrobial proteins.

In other embodiments of the invention, the antimicrobial agent is an antiseptic agent. Several antiseptic agents are known in the art and these include a taurinamide derivative, a phenol, a quaternary ammonium surfactant, a chlorine-containing agent, a quinaldinium, a lactone, a dye, a thiosemicarbazone, a quinone, a carbamate, urea, salicylamide, carbanilide, a guanide, an amidine, an imidazoline biocide, acetic acid, benzoic acid, sorbic acid, propionic acid, boric acid, dehydroacetic acid, sulfurous acid, vanillic acid, esters of p-hydroxybenzoic acid, isopropanol, propylene glycol, benzyl alcohol, chlorobutanol, phenylethyl alcohol, 2-bromo-2-nitropropan-1,3-diol, formaldehyde, glutaraldehyde, calcium hypochlorite, potassium hypochlorite, sodium hypochlorite, iodine (in various solvents), povidone-iodine, hexamethylenetetramine, noxythiolin, 1-(3-choroallyl)-3,5, 7-triazo 1-azoniaadamantane chloride, taurolidine, taurultam, N(5-nitro-2-furfurylidene)-1-amino-hydantoin, 5-nitro-2-furaldehyde semicarbazone, 3,4,4'-trichlorocarbanilide, 3,4',5-tribromosalicylanilide, 3-trifluoromethyl-4,4'-dichlorocarbanilide, 8-hydroxyquinoline, 1-cyclopropyl-6-fluoro-1,4-dihydro-4-oxo-7-(1-piperazinyl)-3-quinolinecarboxylic acid, 1,4-dihydro-1-ethyl-6-fluoro-4-oxo-7-(1-piperazinyl)-3-quinolinecarboxylic acid, hydrogen peroxide, peracetic acid, phenol, sodium oxychlorosene, parachlorometaxylenol, 2,4,4'-trichloro-2'-hydroxydiphenol, thymol, chlorhexidine, benzalkonium chloride, cetylpyridinium chloride, silver sulfadiazine, or silver nitrate.

In some embodiments of the invention, the antiseptic agent is as set forth in the specification of U.S. Provisional Application Ser. No. 60/261,447, U.S. Provisional Application Ser. No. 60/316,165, and U.S. Non-Provisional patent application Ser. No. 10/044,842, incorporated herein by reference in their entirety. Thus, in some embodiments the antiseptic agent comprises a basic reagent and a dye.

The basic reagent may be a guanidium compound, a biguanide, a bipyridine, a phenoxide antiseptic, an alkyl oxide, an aryl oxide, a thiol, a halide, an aliphatic amine, or an aromatic amine. In some specific aspects, the basic reagent is a guanidium compound. Non-limiting examples of guanidium compounds include chlorhexidine, alexidine, hexamidine. In other specific embodiments, the basic reagent is a bipyridine. One example of a bipyridine is octenidine. In yet other aspects, the basic reagent is a phenoxide antiseptic.

The dye may be a triarylmethane dye, a monoazo dye, a diazo dye, an indigoid dye, a xanthene dye, an anthraquinone dye, a quinoline dye, an FD&C dye. Non-limiting examples of triarylmethane dye include gentian violet, crystal violet, ethyl violet, or brilliant green. Exemplary monoazo dyes inlude FD&C Yellow No. 5, or FD&C Yellow No. 6. Other non-limiting examples of FD&C dye include Blue No. 1 or Green No. 3. One non-limiting example of diazo dyes is D&C Red No. 17. An example of an indigoid dye is FD&C Blue No. 2. An examples of a xanthene dye is FD&C Red No. 3; of an anthraquinone dye is D&C Green No. 6; and of an quinoline dye is D&C Yellow No. 1.

Other examples of antiseptics that may be used to prepare the antimicrobial solutions of the invention are the phenoxide antiseptics such as clofoctol, chloroxylenol or triclosan. Still other antiseptic agents that may be used to prepare the amntimicrobial solutions of the invention are gendine, genlenol, genlosan, or genfoctol.

One of skill in the art will appreciate that one can use one or more of the antimicrobial agents including one or more antibacterial agent, and/or one or more antifungal agent, and/or one or more antiviral agent, and/or one or more antiseptic agent, and/or combinations thereof.

A wide variety of chelator agents are contemplated as useful in preparing the antimicrobial solutions of the invention. This includes chelators such as EDTA free acid, EDTA 2Na, EDTA 3Na, EDTA 4Na, EDTA 2K, EDTA 2Li, EDTA 2NH$_4$, EDTA 3K, Ba(II)-EDTA, Ca(II)-EDTA, Co(II)-EDTA Cu(II)-EDTA, Dy(III)-EDTA, Eu(III)-EDTA, Fe(III)-EDTA, In(III-EDTA, La(III)-EDTA, CyDTA, DHEG, diethylenetriamine penta acetic acid (DTPA), DTPA-OH, EDDA, EDDP, EDDPO, EDTA-OH, EDTPO, EGTA, HBED, HDTA, HIDA, IDA, Methyl-EDTA, NTA, NTP, NTPO, O-Bistren, TTHA, EGTA, DMSA, deferoxamine, dimercaprol, zinc citrate, a combination of bismuth and citrate, penicillamine, succimer or Etidronate. It is contemplated that any chelator which binds barium, calcium, cerium, cobalt, copper, iron, magnesium, manganese, nickel, strontium, or zinc will be acceptable for use in the present invention.

Alternatively, one may use at least one anticoagulant such as heparin, hirudin, EGTA, EDTA, urokinase, streptokinase, hydrogen peroxide etc., in the preparation of the antimicrobial solutions of the invention.

A variety of alcohols are contemplated as useful in the preparation of the instant antimicrobial solution, and include any antimicrobially active alcohol. Non-limiting examples of alcohols include ethanol, methanol, isopropanol, propylene glycol, benzyl alcohol, chlorobutanol, phenylethyl alcohol, and the like. The concentration of the alcohol is preferably in the range of 5%-80% (v/v), more preferably in the range of 10% to 50%, more preferably in the range of 15% to 40%, more preferably in the range of 20% to 30%, with the most preferable being about 25%. Thus, the more preferred concentration of alcohol will include 5%, 6%, 7%, 8%, 9%, 10%, 15%, 20%, 25%, 30%, 35%, 40%, 45%, 50%, 55%, 60%, 65%, 70%, 75%, or 80% (v/v) of the alcohol in the preparation of the instant antimicrobial solutions. This includes the use of intermediate concentrations of alcohol such as 11%, 22.5%, 26% and the like.

One of skill in the art will appreciate that the solutions of the instant invention can comprise various combinations of at least one alcohol, at least one antimicrobial agent, and at least one chelator/anticoagulant. In some specific embodiments, the solution of the invention comprises at least one alcohol, at least one tetracycline and at least one chelator/anticoagulant. In a specific aspect, such an antimicrobial solution comprises ethanol, at least one tetracycline and EDTA or heparin.

In other specific aspects, such a solution comprises ethanol, minocycline and EDTA or heparin. In one embodiment of this aspect, the concentration of minocycline is 0.001 mg/ml to 100 mg/ml. In another embodiment, the concentration of minocycline is about 3 mg/ml. In another aspect, the concentration of EDTA is in the range of 10-100 mg/ml. In one embodiment of this aspect, the concentration of EDTA is about 30 mg/ml.

The invention also provides methods for reducing microbial organisms from a surface comprising: a) obtaining an antimicrobial solution of the invention as set forth above; and b) contacting the surface with the antimicrobial solution, whereby said contacting reduces microbial organisms from the surface.

In one embodiment of the method, the contacting is performed for 4 hours or less. In other embodiments of the method, the contacting is performed for 2 hours or less, for 1 hour or less, for 30 minutes or less, or for 15 minutes or less.

In another aspect, the method further comprises eradicating microbes from the surface wherein the contacting is performed for about 15 minutes or more.

The methods of the invention can be used to reduce microbial agents from the surface of a medical device such as a catheter, an endotracheal tube, a nephrostomy tube, a biliary stent, an orthopedic device, a prosthetic valve, a medical implant, dental devices or dental implants, cardiac assist devices, vascular grafts, tracheostomy, ventriclulostomy devices, or intrathecal devices. In some aspects, the catheter is an indwelling catheter such as a central venous catheter, a peripheral intravenous catheter, an arterial catheter, a Swan-Ganz catheter, a hemodialysis catheter, an urinary catheter, a peritoneal catheter, an umbilical catheter, a percutaneous nontunneled silicone catheter, a cuffed tunneled central venous catheter or a subcutaneous central venous port.

In other embodiments, the methods of the invention are useful in reducing microbial agents from a surface such as an organic surface or an inorganic surface. An organic surface is exemplified by skin, surgical sutures, mucosal membrane surface, or an epithelial surface. An inorganic surface may be the surface of a pipe or pipeline, a floor, a table-top, a countertop, hospital equipment, or a wheel chair, etc. Non-limiting examples of a pipe is an oil pipeline, a water pipeline, an ice machine pipe, or a beverage dispensing pipe.

It is contemplated that the antimicrobial solutions of the present invention will find particular usefulness as antimicrobial mouthwash solutions. Such mouthwash solutions are contemplated to be useful both in conjunction with dental procedures and oral sterilization as well as in general dental and oral hygiene applications. Antimicrobial mouthwash is becoming extremely important in the prevention of oral cavity infections as well as aspiration pneumonia. Microbial organisms in the mouth particularly around the teeth, embed themselves in biofilm and the pathogenesis of infection and colonization is similar to that seen in, for example, vascular catheters. In this regard, it is contemplated that one will preferably apply the triple combinations of the present invention, that will include an antimicrobial (possibly antiseptic) with EDTA and low concentration alcohol as a mouthwash or mouth flush solution.

The invention also provides a kit for disinfecting a surface to reduce microorganisms thereon, wherein the kit comprises components including at least one antimicrobial agent, at least one anticoagulant/chelator, and at least one alcohol, contained in a suitable container. The components may be combined in a single container, or powdered components may be lyophilized, combined and separately compartmentalized, or all of the components may be placed in separate containers. In some embodiments, only the antimicrobial agent(s) is included as a dried powder. In aspects comprising powdered components, the kit may optionally include a second carrier solution for reconstituting the lyophilized antibiotic agent(s).

In preferred aspects, the kit will include a unit dose of a pharmacologically effective amount of minocycline and EDTA (or heparin), either provided separately as a lyophilized or powdered dose or already mixed in an ethanol solution. In a specific embodiment, the unit dose contains at least about 9 mg of minocycline and at least about 90 mg of EDTA. Such a kit may further comprise a preselected amount of an ethanol solution such that when the ethanol solution is mixed with the lyophilized unit dose, the concentration of minocycline is 3 mg/ml and the concentration of EDTA is 30 mg/ml.

Kits in accordance with the present invention may be used to reduce/eliminate microbes on the surface of a medical device, a pipe or pipeline, a floor, a table-top, a counter-top, hospital equipment, or a wheel chair. It is also contemplated that the kits of the invention will further comprise a means for introducing the kit components into the medical device, the pipe or surface.

In some specific aspects of the invention, a syringe or vial comprising a lyophilized unit dose of a pharmacologically effective amount of one or more of the three components of the flush solutions of the present invention. For example, such a syringe may comprise minocycline and EDTA (or heparin) mixed in an ethanol solution. In a specific embodiment, the unit dose contains at least about 9 mg of minocycline and at least about 90 mg of EDTA. Such a syringe or vial may further comprises a preselected amount of an ethanol solution such that when the ethanol solution is mixed with the lyophilized unit dose, the desired concentration of the particular agent is obtained, such as about 3 mg/ml in the case of minocycline and about 30 mg/ml. in the case of EDTA.

In other embodiments of the invention, a locking solution for filling and/or flushing a medical indwelling device such as, but not limited to, an implanted catheter is contemplated. The locking solution may comprise at least one antimicrobial agent, at least one chelator and/or anticoagulant, and at least one alcohol.

Some of the terms used in the present application are defined below:

An "antimicrobial agent" is defined herein as an agent that has antibiotic properties against bacteria, fungi, viruses and other pathogens and includes antibacterial agents, antifungal agents, antiviral agents and antiseptic agents.

As used herein, the term "antifungal agent" is defined as a compound having either a fungicidal or fungistatic effect upon fungi contacted by the compound. As used herein, the term "fungicidal" is defined to mean having a destructive killing action upon fungi. As used herein, the term "fungistatic" is defined to mean having an inhibiting action upon the growth of fungi.

As used herein, the term "antibacterial agent" is defined as a compound having either a bactericidal or bacteriostatic effect upon bacteria contacted by the compound. As used herein, the term "bactericidal" is defined to mean having a destructive killing action upon bacteria. As used herein, the term "bacteriostatic" is defined to mean having an inhibiting action upon the growth of bacteria.

As used herein, the term "antiviral agent" is defined as a compound that can either kill viral agents or one that stops the replication of viruses upon contact by the compound.

For the purposes of this disclosure, the phrase "effective amount" or "therapeutically effective amount" is defined as a dosage sufficient to induce a microbicidal or microbistatic effect upon the microbes contacted by the composition on a surface.

The phrase "a chelator" denotes one or more chelators. As used herein, the term "chelator" is defined as a molecule comprising nonmetal atoms, two or more of which atoms are capable of linking or binding with a metal ion to form a heterocyclic ring including the metal ion.

As used herein the terms "contact", "contacted", and "contacting", or "exposed" and "exposure" are used to describe the process by which any of the compositions disclosed in the present invention, comes in direct juxtaposition with the surface of a medical device or any other surface from which microbial growth is to be reduced or eradicated.

As used herein in the specification, "a" or "an" may mean one or more. As used herein in the claim(s), when used in conjunction with the word "comprising", the words "a" or "an" may mean one or more than one. As used herein "another" may mean at least a second or more.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
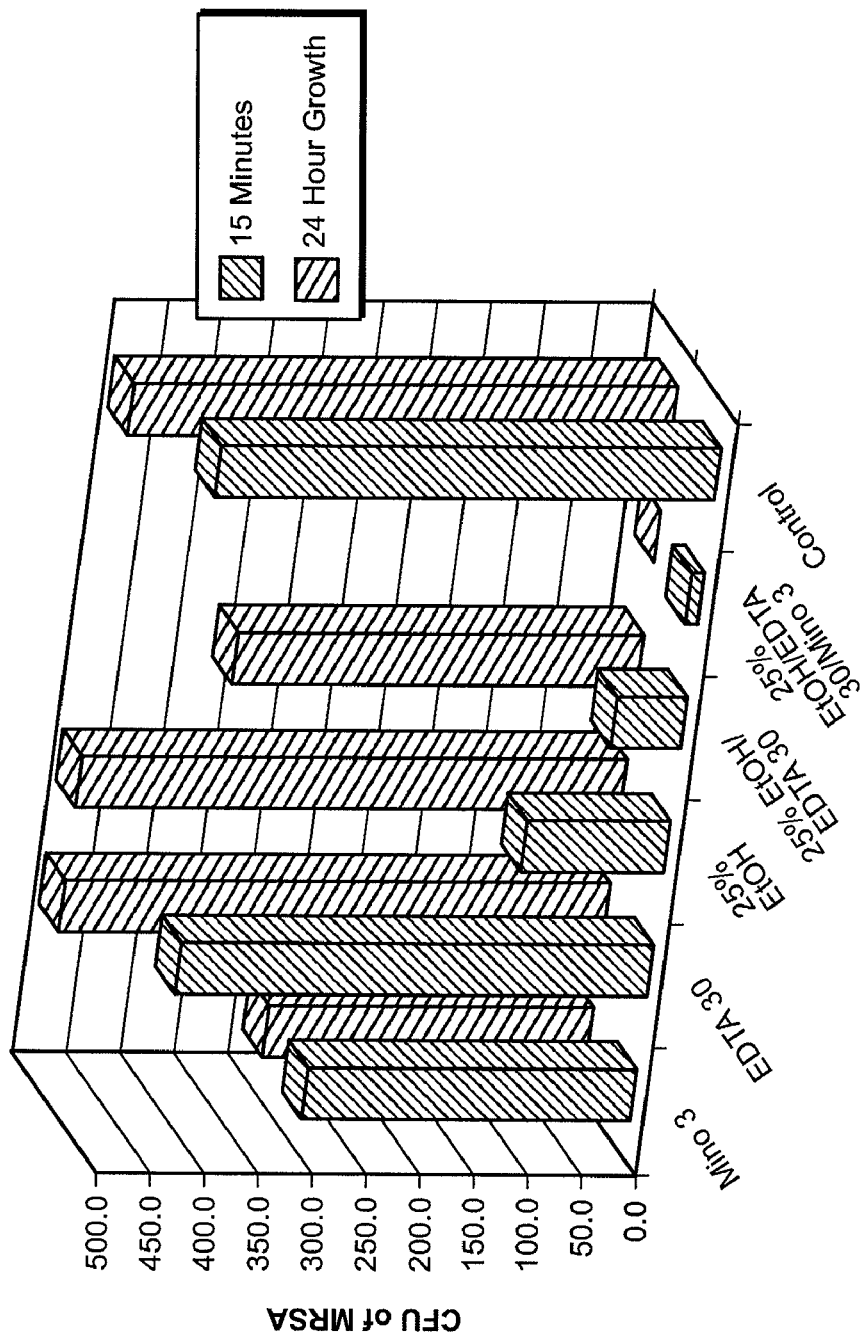
FIG. 1. Ethanol in combination with M-EDTA as a flush solution used for 15 minutes or 24 hours, as indicated, tested against MRSA in biofilm.

Microorganisms that attach themselves to inert surfaces, such as medical devices including, vascular catheters, endotracheal tubes, Foley catheters, biliary stents, nephrostomy tubes, prosthetic valves, ventriculostomy or epidural catheters, or fluid pipelines, such as oil pipelines or water pipelines, produce a layer made of exopolysaccharide called microbial biofilm. These organisms embed themselves in this layer. This biofilm layer ultimately becomes the protective environment that shields these organisms on the inert surface from the antimicrobial activity of various antibiotics or antiseptics. In U.S. Pat. Nos. 5,362,754 and 5,688,516, incorporated herein by reference in their entirety, the present inventor demonstrated that a combination of one or more antimicrobial agent with one or more chelator and/or anticoagulant (such as EDTA or heparin) reduces or eradicates these antibiotic-resistant biofilm embedded microorganisms if the antimicrobial and chelator combination is allowed to dwell on the surface for at least 4 hours. However, in both clinical and environmental situations, it is typically not feasible to allow a 4 hour dwell time for the chelator and antimicrobial agent to reduce or eradicate the microbes. For example, it is not possible to interrupt the therapy of critically ill patients receiving continuous infusion therapy through a vascular catheter for 4 hours. It is also not possible to interrupt an environmental situation involving fluid pipelines for 4 hours to allow for such a prolonged dwell time of antimicrobial/chelator solution.

A. The Present Invention

The present invention allows rapid reduction and/or eradication of microorganisms embedded in a biofilm in a time as short as about 15 minutes of exposure to combinations of at least one antimicrobial and at least one chelator/anticoagulant, if this combination is prepared in an alcohol. This is exemplified in one embodiment by minocycline-EDTA in an ethanol solution, which is described in detail in the application. However, one of skill in the art will recognize that one may use any antimicrobial agent, any chelator/anticoagulant and any alcohol.

In addition, the present invention provides antimicrobial solutions comprising one or more antimicrobial agents, one or more chelator/anticoagulant, and an alcohol solution. The present invention also provides methods for the rapid reduction or eradication of microorganisms embedded in a biofilm on a surface comprising contacting or exposing the surface to a flush solution of the invention. Thus, the invention provides methods for reducing or eradicating microbes from the surfaces of medical devices, including indwelling medial devices, as well as other surfaces, pipelines and the like.

The compositions and the methods of the present invention have an unexpected and surprising efficacy not provided by compositions that comprise only alcohol solutions, or compositions that comprise combinations of antimicrobials with chelators/anticoagulants. In one specific example, the combination of the antimicrobial agent minocycline with the chelator/anticoagulant EDTA requires about 4 hours of exposure or dwell time to reduce microbes from the surface of a medical device. On the other hand, a 25% ethanol solution alone suppresses colonizing organisms embedded in biofilm, but does not eradicate them. However, one exemplary composition of the present invention, comprising minocycline, EDTA and 25% ethanol provides rapid reduction and/or eradication of the microbial organisms within 15 minutes of exposure and also prevents the re-growth of the microbes.

1. Medical Applications

One of the applications of the antimicrobial flush solutions of the invention is to reduce or eradicate microbes from the surfaces of medical devices especially indwelling medical devices such as catheters, endotracheal tubes, nephrostomy tubea, biliary stents, orthopedic devices, prosthetic devices, and medical implants.

There are at least 5 million central venous catheters inserted annually in the United States, 1.5 million of which are long-term catheters that remain in place for an average of 100 days, and at least 3.5 million short-term catheters that remain for an average of 7 days. All of these venous catheters are flushed with heparin on a daily basis. It is estimated that at least 150-175 million catheter flushes occur annually in the United States alone. Heparin has good anticoagulant activity and, hence, prevents thrombotic occlusions. However, heparin has no antimicrobial activity and, in fact, given the alkaline media that heparin creates, it has been shown to be a promoter of microbial colonization of catheter surfaces. Irrespective of whether heparin is used, almost 90%-100% of indwelling vascular catheters end up being colonized with organisms embedded in biofilm on the surface of these devices, particularly at the lumenal surface. Hence, the most serious and frequent complication of vascular catheters is infection, whereby as fluid is flushed through the lumen of the catheter, microorganisms migrate into the bloodstream and cause catheter-related bloodstream infections. Indwelling central venous catheters are associated with around 5%-8% frequency of catheter-related bloodstream infection, which in turn is associated with an attributable mortality of 25% in critically ill patients. Such an event is also associated with high morbidity and a cost per episode of an average of $30,000.

EDTA is a well-known chelator of iron and calcium, as well as an active anticoagulant used in blood collection tubes. EDTA has been shown to have equivalent anticoagulant activity to heparin. In addition, EDTA has antibiofilm activity and enhances the antimicrobial activity of other antimicrobial agents, such as minocycline. However, for a combination of an antmicrobial with a chelator (such as minocycline-EDTA) to eradicate organisms embedded in biofilm, contacting the surface for at least 4-hour with this combination is required. This is demonstrated in U.S. Pat. No. 5,362,754 (see especially data in Tables 3, 4 and 5) and in U.S. Pat. No. 5,688,516, (see especially columns 15 and 16 and Tables 3, 4 and 5). This prolonged period of contacting or dwell time is not possible in the highest risk patient population (i.e., in patients receiving total parental nutrition or critically ill patients), as these patients require a continuous, often uninterrupted, infusion through the catheter. In order to allow for a rapid reduction or eradication of microorganisms, an improvement has been developed in the present invention wherein the antimicrobial(s) and chelator(s)/anticoagulant(s) is prepared in an alcohol solution. In one example, this is embodied by aminocycline-EDTA combination in a 25% ethanol solution.

The present invention, thus, provides that indwelling medical devices such as catheters be flushed with this antimicrobial and chelator/anticoagulant in an alcohol-based solution. This will provide chelation/anticoagulation through the chelator (such as EDTA). In addition, the combination of antibiotic/chelator with an alcohol results in broad-spectrum reduction or eradication of microbial organisms embedded in biofilm. The alcohol further increases the efficacy of the combination.

Some examples of indwelling medical devices that may be treated with the solutions of the present invention include abdominal cavity drainage bags, connectors and tubing used by colostomy patients, vascular shunts, orthopedic, intraocular, or penile prosthesis devices. Angioplasty devices, heart valves and cardiac pacemakers also are included within the present invention. Catheters such as urinary, venous, arterial, and peritoneal catheters may be treated with the flush solutions of the invention. In addition, tracheotomy devices, shunts, surgical sutures, and other medical devices or prosthesis can be treated.

Furthermore, the medical devices which are amenable to coatings of the compositions of the invention generally have surfaces composed of thermoplastic or polymeric materials such as polyethylene, Dacron, nylon, polyesters, polytetrafluoroethylene, polyurethane, latex, silicone elastomers and the like. Devices with metallic surfaces are also amenable to coatings with the antibiotic combinations. Such devices are exemplified by bone and joint prosthesis. It is also contemplated that the solutions of the invention will be used to disinfect organic surfaces such as skin as well as mucosal surfaces.

An antimicrobial locking solution of the present invention may comprise at least one alcohol, at least one antimicrobial agent and at least one chelator and/or anticoagulant. Various antimicrobial substances as disclosed herein and that are well known to one of ordinary skill in the art may be combined with the locking solution in order to inhibit infection. The antimicrobial locking solution of the present invention may be use for filling or flushing a medical device such as an indwelling device such as an implanted catheter. Other medical devices that are contemplated for use in the present invention are disclosed herein.

2. Environmental Applications

Other than reduction/eradication of microbes in medical devices, the flush solutions of the present invention are also useful in the eradication of the surfaces of other surfaces that microbes can grow on such as pipes, pipelines etc. Fluid pipelines, such as oil and water pipelines, are often obstructed by lumenal biofilm that is produced by microorganisms that colonize the internal surface of these pipelines. Often these pipelines are flushed with antimicrobial agents. However, antimicrobial and antiseptic agents have little activity against organisms embedded in biofilm. Tons of antibiotics, such as gentamicin, are often used to flush the lumen of oil pipelines, to no avail. The present invention provides new and effective compositions and methods for the eradication of organisms, as well as biofilm embedding the lumen of pipelines (oil, water), as well as other devices, such as ice machines. These pipelines or machines can be flushed or rinsed with the compositions of the invention that comprise at least one antimicrobial agent and at least one chelator or anticoagulant prepared in a base solution of ethanol. Flushing the pipelines, machines or tubes with the compositions of the invention provide rapid reduction and/or eradication of the biofilm and the organisms in biofilm thereby preventing any obstruction or contamination of the water, oil or the ice machines in certain environmental settings.

B. Antimicrobial Agents and Microbes

The present compositions are contemplated to have one or more antimicrobial agents. "Antimicrobial agents" are defined herein as antibacterial agents, antifungal agents, antiviral agents and/or antiseptic agents.

While the invention is not limited to any particular antimicrobial agent some exemplary classes and examples of antibacterial agents, antifungal agents, antiviral agents as well as antiseptic agents are described above in the section entitled "summary of invention." Of course one of skill in the art will appreciate that any combination as well as agents from the different types and classes of the antimicrobial agents can be combined to prepare the solutions of the invention.

Some non-limiting exemplary bacterial and fungal microbes that can be reduced or eradicated by the compositions and methods of the invention include *Staphyloccous* species such as *Staphylococcus epidermidis*, *Staphylococcus aureus*; *Aspergllus* species, such as *Aspergillus flavus*, *Aspergillus terreus*; *Fusarium oxysporum*, *Candida* species, such as *Candida krusei*, *Candida parapsilosis*, *Candida tropicalis*, *Candida albicans* and *Candida glabrata*. In addition, viruses can also be eradicated.

C. Chelators and/or Anticoagulants

A chelate is the type of coordination compound in which a central metal ion is attached by coordinate links to two or more nonmetal atoms in the same molecule. Heterocyclic rings are thus formed during chelation, with the metal atom as part of the ring. The molecule comprising the nonmetal linking atoms is termed a chelator. Chelators are used in various chemical applications, for example as titrating agents or as metal ion scavengers. Chelators can be used to remove ions from participation in biological reactions. For example, the well-known chelator ethylenediamine-N,N,N',N',-tetraacetic acid (EDTA) acts as an anticoagulant because it is capable of scavenging calcium ions from the blood.

It has been previously shown that chelators have significant growth inhibitory effect against several microbes. It is known that iron and other trace metals are essential in the life cycle of microorganisms such as fungi and bacteria. Without these trace metals, microbes are unable to grow and reproduce. Although iron is abundant in nature, its availability for microbial assimilation is limited owing to the insolubility of ferric ions at neutral or alkaline pH. As a consequence, many microbes have evolved their own specialized trace metal-scavenging molecules, called siderophores, which bind with trace metals and make them available for uptake by the microbes. The chelators used in conjunction with the present invention provide an inhibitory effect upon microbial pathogens by competing with the siderophores for any available trace metal ions. In this way, the chelators present in the pharmaceutical preparations of the present invention "steal" the metal ions essential for microbial growth, effectively causing the microbe to "starve to death." The additional antibiotic agents and the ethanol of the compositions of the present invention then come in and attack the weakened microbe, thereby destroying them or inhibiting their growth.

Table 1 below provides a representative list of chelators useful in conjunction with the present invention. However, the list provided in Table 1 is not meant to be exhaustive. Preferred chelators are those which bind trace metal ions with a binding constant ranging from $10^1$ to $10^{100}$. More preferred chelators are those which bind trace metal ions with a binding constant ranging from $10^{10}$ to $10^{80}$; and most preferred chelators are those which bind trace metal ions with a binding constant ranging from $10^{15}$ to $10^{60}$. Furthermore, preferred chelators are those which have been shown to have an inhibitory effect upon target microbial pathogens, for example the disodium salt of EDTA.

TABLE 1

Chelators

| Abbreviation | Full Name |
| --- | --- |
| EDTA free acid | Ethylenediamine-N,N,N',N',-tetraacetic acid |
| EDTA 2Na | Ethylenediamine-N,N,N',N',-tetraacetic acid, disodium salt, dihydrate |
| EDTA 3Na | Ethylenediamine-N,N,N',N',-tetraacetic acid, trisodium salt, trihydrate |
| EDTA 4Na | Ethylenediamine-N,N,N',N'-tetraacetic acid, tetrasodium salt, tetrahydrate |
| EDTA 2K | Ethylenefisminr-N,N,N',N'-tetraacetic acid, dipotassium salt, dihydrate |
| EDTA 2Li | Ethylenediamine-N,N,N',N'-tetraacetic acid, dilithium salt, monhydrate |
| EDTA 2NH$_4$ | Ethylenediamine-N,N,N',N'-tetraacetic acid, diammonium salt |
| EDTA 3K | Ethylenediamine-N,N,N',N'-tetraacetic acid, tripotassium salt, dihydrate |
| Ba(II)-EDTA | Ethylenediamine-N,N,N',N'-tetraacetic acid, barium chelate |
| Ca(II)-EDTA | Ethylenediamine-N,N,N',N'-tetraacetic acid, calcium chelate |
| Ce(III)-EDTA | Ethylenediamine-N,N,N',N'-tetraacetic acid, cerium chelate |

TABLE 1-continued

Chelators

| Abbreviation | Full Name |
|---|---|
| Co(II)-EDTA | Ethylenediamine-N,N,N',N'-tetraacetic acid, cobalt chelate |
| Cu(II)-EDTA | Ethylenediamine-N,N,N',N'-tetraacetic acid, copper chelate |
| Dy(III)-EDTA | Ethylenediamine-N,N,N',N'-tetraacetic acid, dysprosium chelate |
| Eu(III)-EDTA | Ethylenediamine-N,N,N',N'-tetraacetic acid, europium chelate |
| Fe(III)-EDTA | Ethylenediamine-N,N,N',N'-tetraacetic acid, iron chelate |
| In(III)-EDTA | Ethylenediamine-N,N,N',N'-tetraacetic acid, indium chelate |
| La(III)-EDTA | Ethylenediamine-N,N,N',N'-tetraacetic acid, lanthanum chelate |
| Mg(II)-EDTA | Ethylenediamine-N,N,N',N'-tetraacetic acid, magnesium chelate |
| Mn(II)-EDTA | Ethylenediamine-N,N,N',N'-tetraacetic acid, manganese chelate |
| Ni(II)-EDTA | Ethylenediamine-N,N,N',N'-tetraacetic acid, nickel chelate |
| Sm(III)-EDTA | Ethylenediamine-N,N,N',N'-tetraacetic acid, samarium chelate |
| Sr(II)-EDTA | Ethylenediamine-N,N,N',N'-tetraacetic acid, strontium chelate |
| Zn(II)-EDTA | Ethylenediamine-N,N,N',N'-tetraacetic acid, zinc chelate |
| CyDTA | trans-1,2-Diaminocyclohexane-N,N,N',N'-tetraaceticacid, monohydrate |
| DHEG | N,N-Bis(2-hydroxyethyl)glycine |
| DTPA-OH | 1,3-Diamino-2-hydroxypropane-N,N,N',N'-tetraacetic acid |
| DTPA | 1,3-Diaminopropane-N,N,N',N'-tetraacetic acid |
| EDDA | Ethylenediamine-N,N'-diacetic acid |
| EDDP | Ethylenediamine-N,N'-dipropionic acid dihydrochloride |
| EDDPO | Ethylenediamine-N,N'-bis(methylenephosphonic acid), hemihydrate |
| EDTA-OH | N-(2-Hydroxyethyl)ethylenediamine-N,N',N'-triacetic acid |
| EDTPO | Ethylenediamine-N,N,N',N'-tetrakis(methylenephosponic acid) |
| EGTA | O,O'-bis(2-aminoethyl)ethyleneglycol-N,N,N',N'-tetraacetic acid |
| HBED | N,N-diacetic acid |
| HDTA | 1,6-Hexamethylenediamine-N,N,N',N'-tetraacetic acid |
| HIDA | N-(2-Hydroxyethyl)iminodiacetic acid |
| IDA | Iminodiacetic acid |
| Methyl-EDTA | 1,2-Diaminopropane-N,N,N',N'-tetraacetic acid |
| NTA | Nitrilotriacetic acid |
| NTP | Nitrilotripropionic acid |
| NTPO | Nitrilotris(methylenephosphoric acid), trisodium salt |
| O-Bistren | 7,19,30-Trioxa-1,4,10,13,16,22,27,33-octaabicyclo [11,11,11] pentatriacontane hexahydrobromide |
| TTHA | Triethylenetetramine-N,N,N',N'',N''',N'''-hexaacetic acid |

In addition, as several anticoagulants have similar chelating and hence antimicrobial activity use of anticoagulants such as EGTA, EDTA, heparin, urokinase, streptokinase, low molecular weight heparin, enoxaparin, sodium coumarin, indanedione, anisindione, warfarin, protamine sulfate, antithrombin III, nitrilotriacetic acid, potassium sodium tartrate, potassium hydrogen D-tartrate, L-tartaric acid dipotassium salt, L-tartaric acid disodium salt, L-tartaric acid monosodium salt, tris(carboxymethyl)amine, warfarin, acetylsalicylic acid, ibuprofen, indomethacin, prostaglandins, sulfinpyrazone, streptokinase, urokinase, tissue plasminogen activator, coumarin, protamine sulfate, anti-thrombin III, coumadin, protein C/protein S, nicoumalone, phenprocoumon, hirudin, hirulog, or glycosaminoglycans etc. is also contemplated in the present invention. Moreover, additional chelators, anticoagulants and/or additional agents useful in the practice of the present invention may be found in U.S. Pat. No. 5,688,516, incorporated herein by reference.

D. Alcohols

The flush solutions of the instant invention are contemplated to comprise an alcohol, such as an antiseptic or disinfectant alcohol. Exemplary alcohols include ethanol, methanol, isopropanol, benzyl alcohol, chlorobutanol, phenylethyl alcohol, 2-bromo-2-nitropropan-1,3-diol, and the like. The present invention contemplates any effective concentration of alcohol, but will typically employ a final alcohol concentration in the range of 5%-80% (v/v), more preferably in the range of 10% to 50%, more preferably in the range of 15% to 40%, more preferably in the range of 20% to 30%, with the most preferable being about 25%. Thus, the more preferred concentration of alcohol will include 5%, 6%, 7%, 8%, 9%, 10%, 15%, 20%, 25%, 30%, 35%, 40%, 45%, 50%, 55%, 60%, 65%, 70%, 75%, or 80% (v/v) of the alcohol in the preparation of the instant antimicrobial solutions. This includes the use of intermediate concentrations of alcohol such as 11%, 22.5%, 26% and the like.

Alcohols such as ethanol are long known to have disinfectant properties. In EP1245247 and U.S. Pat. No. 6,350,251, it is reported that the combination of ethanol with EDTA provides a biocidal lock for indwelling medical devices. In contrast, it has also been shown that a combination of ethanol with EDTA is less effective in killing microbes than ethanol alone (Sherertz et al., 2002). Thus, the art is in a flux about the exact role of the combination of ethanol with EDTA.

The present inventor has shown that ethanol alone, while requiring only a relatively short duration of contact, is only partially effective in killing or controlling microbes on the surface of an indwelling medical device or other surface. In contrast, a combination of an antimicrobial agent and a chelator such as EDTA may be effective, yet it requires a somewhat longer duration of contact (e.g., sometimes on the order of 4 hours). However, in the present invention it is shown that the triple combination of an alcohol, an antimicrobial and a chelator/anticoagulant provides unexpectedly effective antimicrobial properties in a very short duration and in addition to eradicating microbes rapidly from a surface they also preventing re-growth of the microbial pathogen on the surface. An additional advantage for the triple combination, as shown in the studies set forth herein below, is that it is effective at eradicating a broader range of microbial organisms (bacteria and fungi), even at the shorter durations of contact with the treated surface.

E. Additional Agents

It is also contemplated that any additional pharmacologically active ingredients or sterilization agents may be comprised in the solutions of the present invention or may be used separately for flushing or treating the devices of the present invention to further reduce or eliminate pathogenic microbes and viruses. Typical pharmacologically active ingredients include antifibrin agents, anti-thrombotic agents, and anti-inflammatory agents. Anti-inflammatory agents include steroids, and nonsteroidal anti-inflammatory agents, and salicylates. Anti-thrombotic drugs including acetylsalicylic acid, dipyridamole, heparin, ibuprofen, indomethacin, prostaglandins, sulfinpyrazone, warfarin, thrombolytic enzymes such as streptokinase, urokinase, or plasminogen activator. Complexing agents such as ammonium-1-pyrrolidine dithiocarbanate may also be used. However, the above examples are not meant to be limiting.

In certain applications, it will be sufficient to provide a single pharmacologically active ingredient in the device. In other situations, it will be desirable to combine compatible ingredients. For example, it may prove useful to provide an antimicrobial agent along with an anticoagulant and/or an anti-inflammatory agent. In another example, it may prove useful to provide multiple antimicrobial agents with differing target specificities, modes of action or duration, either alone or in combination with anticoagulants or antiinflammatory agents.

F. Packaging and Kits

Described herein are various packaging techniques that may be employed in providing the flush solutions of the invention as part of a commercially available kit. The kit will optionally include an instruction sheet insert to identify how the kit is to be used.

The kits described in this section are exemplified by a solution comprising minocycline as the antibiotic, EDTA as the chelator/anticoagulant, and ethanol. However, as will be appreciated by the skilled artisan, any other combination of one or more antibiotic, one or more chelator/anticoagulant, and ethanol as described in the present disclosure may be packaged in a similar manner. The kit may comprise of one or two or three or more compartments. The components of the kit may be provided in separate compartments or in the same compartment. The components of the kit may be provided separately or mixed. The mixed components may contain two or more agents such as an antibiotic, a chelator/anticoagulant, or ethanol, or additional component.

One of the packaging options below maintain the ingredients, for example, the antibiotic, such as minocycline, and the chelating agent/anticoagulant, such as EDTA, in an uncombined form. These components are to be combined shortly before use. These packaging options are contemplated to be part of a 2-compartment or three-compartment container system to provide a total volume of about 3 ml of the ready to use preparation. Any compartmentalized container system may be used to package the compositions of the present invention. An exemplary container system is available from Becton Dickinson.

Option 1: A 3-Compartment system comprising two dry components such as 3-9 mg minocycline (dry), 10-100 mg EDTA (powdered) and one wet component comprising 3 ml diluent (alcohol alone or diluted in saline or distilled water). When ready for use, the dry components, minocycline and EDTA, will be allowed to mix with the diluent. Final concentration of the mixture should be about 3 mg/ml minocycline and 30 mg/ml EDTA.

Option 2: A 2-Compartment system antibiotic and chelator/anticoagulant (one wet, one dry) comprising for example 3-9 mg/ml minocycline and 10-100 mg EDTA. When ready for use, the dry EDTA powder will be combined with the minocycline in solution. The minocycline may be suspended in either saline, distilled water, alcohol solution or other physiologically acceptable diluent. Alternatively, the minocycline may be in a dry powdered form, and the EDTA in solution. A wet/wet® dual chamber container system, available from Becton-Dickinson, may be used in these applications.

Option 3: A 2 compartment system comprising both wet compartments comprising antimicrobial agent(s) and chelator/anticoagulant comprising in one example 10-100 EDTA Solution and 3-9 mg/ml Minocycline Solution where the solution comprises alcohol. When ready for use, the EDTA solution will be combined with minocycline solution. Once combined, the solution will have a concentration of 3 mg/ml minocycline and 30 mg/ml EDTA. A wet/wet® dual chamber container system, available from Becton-Dickinson, may be used in these applications.

Option 4: A 2 compartment system both comprising dry powders of the antimicrobial agent(s) and chelator/anticoagulant in a diluent comprising for example, 10-100 EDTA (dry) and 3-9 mg minocycline (dry) and diluent solution. The dry EDTA and dry minocycline may be suspended in a solution of an alcohol made in either saline, distilled water, or other physiologically acceptable diluent. A liquid/dry® dual container system, from Becton-Dickinson, may be used. When ready for use, the dry minocycline powder will be allowed to combine with the EDTA solution. The EDTA can be suspended in either saline or distilled water, or alcohol solution, or other physiologically acceptable diluent.

The various compartmentalized embodiments of the present invention as disclosed above, may be provided in a kit form. Such kits would include a container means comprising a volume of diluent, comprising an alcohol optionally diluted if required in a solution such as saline or sterile water, a second (or more) container means comprising one or more antimicrobial or biocide, a third (or more) container means comprising one or more chelating/anticoagulant agent. The dry components may optionally be mixed in one compartment. The addition of the diluent would then be performed immediately prior to use.

The container means of the kits will generally include at least one vial, test tube, flask, bottle, syringe or other container means, into which the antimicrobial/chelator/anticoagulant/alcohol may be placed, and preferably, suitably aliquoted. Where a second or third antibiotic agent, other chelator, alcohol, or additional component is provided, the kit will also generally contain a second, third or other additional container into which this component may be placed. The kits of the present invention will also typically include a means for containing the alcohol, antimicrobial agent, chelator/anticoagulant, and any other reagent containers in close confinement for commercial sale. Such containers may include injection or blow-molded plastic, or glass containers into which the desired vials are retained.

G. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Reduction and/or Eradication of Microbes Using the Modified Robbins Device Model In vitro Model of Colonization (Modified Robbins Device). The in vitro model utilized a modified Robbins device (MRD) to study the colonization of catheter segments with organisms embedded in biofilm. The modified Robbins device has been previously described (Nickel et al., 1991; Evans et al., 1987, see also U.S. Pat. No. 5,362,754) and is constructed from an acrylic block, 42 cm long with a lumen of 2×10 mm. It consists of 25 evenly spaced specimen plugs, each connected to a silicone catheter segment (Allegiance Healthcare Corp., McGaw Park, Ill.) whose anterior surface (0.3 cm$^2$) comes in contact with the flushed infusate. After placing the catheter segments in the specimen plug of the modified Robbins device, the entire apparatus was gas sterilized using ethylene oxide. A 500 ml 5% dextrose in water (5% $D_5$/W) was connected to the modified Robbins device through an intravenous tubing administration set and was subsequently infected with an innoculum of $10^8$ CFU/ml of methicillin-resistant *Staphylococcus aureus* (MRSA), to produce an infected infusate at the concentration of $2\times10^5$ CFU/ml. The biofilm-producing *S. aureus* isolates were obtained from patients with CRBSI. In another series of experiments, 500 ml 5% $D_5$/W bag was infected with a biofilm-producing *C. parapsilosis* using an inoculum of $10^5$ CFU/ml to produce an infected infusate at a concentration of $2\times10^2$ CFU/ml of *C. parapsilosis*. The whole system was incubated at 37° C. and the infected infusate was flushed through the MRD using a peristaltic pump permitting the infusate to flow at the rate of 60 ml/hour for 8 hours. The modified Robbins device was left to incubate for a total of 18 hours (another 10 hours). Subsequently, the infected bag was removed and a 250 ml saline sterile bag which was infused through the MRD at 125 ml/hour for 2 hours in order to remove all free floating organisms. To insure biofilm formation, at least three catheter segments were randomly removed from the 25 evenly spaced catheter segments in the MRD and studied by scanning electron microscopy. This was repeated for every organism tested.

Exposure to Anticoagulants/Antimicrobials. The remaining catheter segments were removed and each segment was placed in a tube containing 2 ml of one of the following broth solutions: (1) Mueller-Hinton broth (Becton Dickinson & Co., Cockeysville, Md.); (2) EDTA at a concentration of 30 mg/ml in broth (Abbott Laboratories, North Chicago, Ill.); (3) minocycline at 3 mg/ml in broth (Wyeth-Ayerst Laboratories, Collegeville, Pa.); (4) minocycline (3 mg/ml) and EDTA combination (M-EDTA) in broth; (5) 25% ethanol (ETOH) solution in broth; (6) minocycline at 3 mg/ml in 25% ethanol solution in broth; (7) EDTA 30 mg/ml in 25% ethanol solution in broth; and (8) M-EDTA in 25% ethanol solution in broth. The experiments were repeated in triplicate or quadruplicate, and during each experiment, 2-5 catheter segments were exposed to the same solution for only 15 minutes at 37° C. Subsequently, some of the catheter segments were immediately removed and cultured by scrape sonication. Other alternating catheter segments were removed, placed in broth (TSB), incubated for 24 hours, and then cultured by scrape sonication. This added step of re-incubating catheter segments in broth after the 15 minutes exposure was done to determine whether these agents suppressed the growth of organisms embedded in biofilm or eradicated them. The surface of the catheter segment that was exposed to the infected infusate was scraped with a sterile wooden applicator stick and placed, along with the stick, in a tube containing 0.5 ml of trypticase soy broth. The tubes were sonicated for five minutes; 0.1 ml of the sonicated broth solution in the tube was pipetted and plated over a blood agar plate, which was incubated at 37° for 24 hours. The agar plates were checked for any contaminants. The isolated organisms had to be of the same species and colonial morphology as the original organism used to infect the infusate. The number of colonies quantitated from the agar plate was multiplied by five to correct for the dilution factor and to determine the total number of colonies isolated from a particular catheter segment. A confluent growth of 100 or greater was calculated as $\geq 500$ colonies.

Definitions. Inhibitory activity or suppression is defined as no growth of microbial organisms immediately after 15 minute exposure to the antimicrobial solution. However, regrowth of the organisms after 24 hours incubation in broth was observed.

Eradication is defined as no growth of organisms after immediate 15 minutes exposure to the antimicrobial solution with no subsequent growth upon reincubation for 24 hours in broth.

Results

As shown in Table 2, EDTA alone failed to eradicate methicillin-resistant *S. aureus* and *C. parapsilosis* organisms embedded in biofilm after 15 minutes of exposure, resulting in re-growth after 24 hours of incubation of the catheter segments in broth solution. Minocycline alone (at a concentration of 3 mg/ml) with or without EDTA resulted in some decrease in colonization. However, organisms continued to grow after 15 minutes of exposure and after 24 hours re-incubation in broth at 37° C. A 25% ethanol solution suppressed growth initially to a mean concentration level of 138 colony forming units (CFU). However, upon re-incubation in broth at 37° C. for 24 hours, there was complete re-multiplication and growth of the staphylococcal organisms embedded in biofilm to a high level of 500 CFU per catheter segment, which is comparable to the growth of control catheter segments. The combination of EDTA and 25% ethanol solution resulted in a significant decrease in colonization immediately after 15 minutes of exposure to this solution. However, regrowth occurred after re-incubation in broth solution at 37° C. for an additional 24 hours. Minocycline in 25% ethanol, with or without EDTA, resulted in complete eradication of microorganisms embedded in biofilm after 15 minutes of exposure to the solutions. In addition, re-incubation of the catheter segments in broth for an additional 24 hours at 37° C. failed to allow regrowth of the organisms, verifying the complete eradication of the *S. aureus* organisms embedded in biofilm.

TABLE 2

Modified Robbins Device MRSA Model

| Drug Combination Tested | 15 minutes in Drug mean CFU MRSA | 24 h growth after 15 min in drug mean CFU MRSA |
|---|---|---|
| 3 mg/ml minocycline | 323.7 ± 199.0 | 308.3 ± 151.1 |
| 30 mg/ml EDTA | 479.6 ± 44.9 | 500.0 ± 0.0 |
| 25% EtOH in MHB | 138.0 ± 193.8 | 500.0 ± 0.0 |
| 3 mg/ml minocycline/30 mg/ml EDTA | 295.0 ± 182.0 | 170.8 ± 149.1 |
| 25% EtOH/30 mg/ml EDTA | 25.8 ± 63.5 | 333.9 ± 234.9 |
| 25% EtOH/3 mg/ml minocycline | 0 | 0 |
| 25% EtOH/30 mg/ml EDTA/3 mg/ml minocycline | 0 | 0 |
| Control (MH Broth alone) | 440.3 ± 113.4 | 500.0 ± 0.0 |

As shown in Table 3, EDTA alone, minocycline alone and M-EDTA failed to eradicate *C. parapsilosis* organisms embedded in biofilm. A 25% ethanol solution with or without minocycline, inhibited *C. parapsilosis* growth after 15 minutes of exposure. However, regrowth was noted after 24 hours incubation in broth. EDTA in 25% ethanol and M-EDTA in 25% ethanol completely eradicated *C. parapsilosis* in biofilm after 15 minutes exposure with no regrowth after reincubation in broth.

TABLE 3

Modified Robbins Device *Candida Parapsilosis* Model

| Drug Combinations Tested | 15 Minutes in Drug Mean CFU *C. Parapsilosis* | 24 h Growth after 15 Minutes in Drug Mean CFU *C. Parapsilosis* |
|---|---|---|
| 3 mg/ml minocycline | 138.3 ± 111.8 | 500.0 ± 0.0 |
| 30 mg/ml EDTA | 160 ± 78.8 | 500.0 ± 0.0 |
| 25% EtOH in MHB | 0 | 142.9 ± 225.9 |
| 3 mg/ml minocycline/30 mg/ml EDTA | 152.5 ± 161.3 | 500.0 ± 0.0 |
| 25% EtOH/30 mg/ml EDTA | 0 | 0 |
| 25% EtOH/3 mg/ml minocycline | 0 | 83.3 ± 186.3 |
| 25% EtOH/30 mg/ml EDTA/3 mg/ml minocycline | 0 | 0 |
| Control (MH Broth alone) | 500.0 ± 0.0 | 500.0 ± 0.0 |

Minocycline alone, EDTA alone or the combination of minocycline and EDTA failed to eradicate organisms embedded in biofilm after a rapid exposure of only 15 minutes. 25% ethanol solution also failed to eradicate organisms embedded in biofilm and a high level of regrowth was apparent after catheter segments were re-incubated in broth for an additional 24 hours at 37° C.

The combination of ethanol/EDTA did achieve inhibition or suppression of organisms embedded in biofilm after 15 minutes of exposure of the catheter surfaces to this solution. However, regrowth was noted upon re-incubation of the catheter segments in broth for 24 hours at 37° C. The combination of EDTA/25% ethanol, however, was superior in its inhibitory activity when compared to 25% ethanol alone.

The combination of minocycline in 25% ethanol with or without EDTA was highly active in eradicating organisms embedded in biofilm after 15 minutes of exposure to this combination. Regrowth of *C. parapisilosis* occurred occasionally after exposure to minocycline in 25% ethanol. Regrowth failed to occur after exposure to M-EDTA in 25% ethanol, verifying the complete eradication of *S. aureus* organisms embedded in biofilm after rapid exposure to this triple combination.

Because EDTA has anticoagulant activity and, in these experiments, seems to have added to the antimicrobial activity of 25% ethanol, it was prudent to use the triple combination of minocycline/EDTA in 25% ethanol as a flush or antibiotic lock solution of central venous catheters. In contrast, vancomycin alone or in combination with heparin failed to eradicate microbial organisms embedded in biofilm from catheter surfaces, even after a dwell time of 4-24 hours (see U.S. Pat. No. 5,362,574, columns 11 and 12, Tables 3, 4 and 5.)

Example 2

Testing M-EDTA in 25% Ethanol Using the Silicone Disk Bioprosthetic Colonization In Vitro Model The inventor next determined the efficacy of minocycline and EDTA combination in 25% ethanol in eradicating staphylococci and candida embedded in biofilm. Prevention of regrowth after reincubation was assessed using a novel silicone disk bioprosthetic colonization model. The procedure is described below.

Experimental Procedure

On day 1, pieces of biofilm were prepared. Sterile (Ethylene Oxide Gas Sterilized) silicone disks were placed in 5 ml sterile snap top Falcon tubes and 0.5 ml of pooled plasma added. This was followed by incubation (while rocking) overnight at 37° C.

On day 2, the bacteria was added to form the biofilm. Using sterile plastic transfer pipettes, the plasma was suctioned out from the tubes and replaced with 0.5 ml of bacterial inoculum (50 ml of Mueller-Hinton broth containing 4-5 colonies of freshly grown bacteria). The tubes were incubated overnight at 37° C.

On day 3, a drug was added in an attempt to kill the bacteria. Before adding the drug, the pieces were washed in 0.5 ml of 0.9% saline in order to remove any planktonic bacteria. The tubes (containing the biofilm disks and saline) were placed in the incubator at 37° C. for 30 minutes. The saline was then pipetted out using sterile plastic transfer pipettes (taking care not to disturb the pieces too much). The silicone disks were then transferred to new 5 ml snap-top falcon tubes containing 0.5 ml of the drug solution to be tested. The drug solutions tested were as follows: (1) minocycline 3 mg/ml; (2) EDTA 30 mg/ml; (3) 25% ethanol solution; (4) EDTA 30 mg/ml in 25% ethanol; (5) minocycline 3 mg/ml in 25% ethanol; (6) minocycline 3 mg/ml with EDTA 30 mg/ml; and (7) triple combination of minocycline 3 mg/ml and EDTA 30 mg/ml in 25% ethanol solution. The disks were allowed to sit in the drug for 1 hour. The drug was then suctioned out using a plastic transfer pipette. The pieces were once again washed with 0.5 ml saline (added, and shaken for 30 seconds). The disks were then transferred to 15 ml snap-top falcon tubes containing 5 ml of 0.9% saline. The pieces were sonicated for 5 minutes, and then vortexed for 30 seconds. 100 microliters (µl) of the saline was then plated on a room temperature TSAII blood agar plate, and evenly spread using a sterile glass spreader. The plates were incubated overnight at 37° C.

For the 24 hour reincubation studies, pieces of biofilm were prepared the same exact way as the regular pieces. Before adding the drug, the pieces were washed in 0.5 ml of 0.9% saline in order to remove any planktonic bacteria. The tubes (now containing the biofilm disks and saline) were placed in the incubator at 37° C. for 30 minutes. The saline was then pipetted out using sterile plastic transfer pipettes (taking care not to disturb the pieces too much). The silicone disks were then transferred to new 5 ml snap-top falcon tubes containing 0.5 ml of the drug to be tested. The disks were allowed to sit in the drug for 15 minutes. The drug was then suctioned out using a plastic transfer pipette. The pieces were once again washed with 0.5 ml saline (added, and shaken for 30 seconds). The pieces were then transferred to new sterile 5 ml snap-top falcon tubes containing 0.5 ml of sterile trypticase soy broth (TSB) and then placed in the incubator at 37° C. overnight.

On day 4, colonies were counted and the results recorded. The colonies were hand counted, and counting was stopped at 100 colonies. Anything greater was considered >100 colonies. The counts were recorded, and multiplied by a factor of 50 because of the dilution factor between the 5 ml of saline containing the disk and the 100 µl that was plated onto the TSAII blood agar plates. The pieces were then sonicated (in the same TSB that grew overnight) for 5 minutes. 100 µl was then plated on TSAII blood agar plates, and the plates were placed in the incubator to grow overnight at 37° C.

On day 5, the regrowth pieces were counted. The colonies were hand counted, and counting was stopped at 100 colonies. Anything greater was considered >100 colonies. The counts were recorded, and multiplied by a factor of 5 because of the dilution factor between the 0.5 ml of TSB containing the disk and the 100 µl that was plated onto the TSAII blood agar plates.

Results

The silicone disk bioprosthetic colonization model has been previously described by Kuhn et al. (2002). This in vitro model is more clinically relevant than the modified Robin device, in vitro model, in that it allows the silicone disk segments to be immersed in serum prior to exposing to high inoculum of bacteria or fungi. Furthermore, it allows a higher concentration of adherence of bacteria and fungi on the silicone disk of up to 5,000 CFU/disk (the modified Robbins device allows for only 500 CFU/latex catheter segment). Because of the high inoculum that the silicone disk segments were exposed to in the bioprosthetic colonization model, the various disk segments were exposed to the various antimicrobial agents for one hour (rather than 15 minutes in the modified Robbins device). The results were consistent with the findings and observations in the modified Robbins device model. As shown in Table 4, exposure to either minocycline alone or EDTA or ethanol, or the combination of minocycline and EDTA, failed to suppress the bioprosthetic MRSA colonization of the silicone disks. EDTA in 25% ethanol had some partial suppression but there was regrowth of the organisms after 24 hour incubation. As expected, the control silicone disk segments were heavily colonized before and after 24 hour reincubation. Minocycline in 25% ethanol was highly suppressive but there was regrowth after 24 hour incubation. However, the triple combination of M-EDTA in 25% ethanol was unique in completely eradicating the MRSA organisms, with complete inhibition of regrowth after 24 hours of incubation.

TABLE 4

Silicone Disk Bioprosthetic Colonization MRSA Model

| Drug Combinations Tested | 1 hour in Drug Mean CFU ± std. error | 24 h Growth after 1 hour in Drug Mean CFU ± std. error |
| --- | --- | --- |
| 3 mg/ml minocycline n = 5 | 5000.0 ± 0.0 | 5000.0 ± 0.0 |
| 30 mg/ml EDTA n = 5 | 5000.0 ± 0.0 | 5000.0 ± 0.0 |
| 25% EtOH in MHB n = 10 | 2900.0 ± 722.8 | 5000.0 ± 0.0 |
| 3 mg/ml minocycline/30 mg/ml EDTA n = 10 | 5000.0 ± 0.0 | 3110.0 ± 637.6 |
| 25% EtOH/30 mg/ml EDTA n = 10 | 730.0 ± 379.3 | 2770.0 ± 785.7 |
| 25% EtOH/3 mg/ml minocycline n = 10 | 0 | 85.0 ± 85.0 |
| 25% EtOH/30 mg/ml EDTA/3 mg/ml minocycline n = 10 | 0 | 0 |
| Control (MH Broth alone) n = 10 | 5000.0 ± 0.0 | 5000.0 ± 0.0 |

Table 5 shows a similar trend for *Candida parapsilosis*. Minocycline alone, EDTA alone, or the combination of M-EDTA failed to suppress or eradicate the growth of *Candida parapsilosis* on silicone disks. Furthermore, there was a heavy regrowth of the *C. parapsilosis* on silicone disks after exposure to these agents and reincubation for 24 hours. Twenty-five percent ethanol alone, EDTA in 25% ethanol or minocycline in 25% ethanol failed to completely suppress *Candida parapsilosis* growth after one hour exposure and there was heavy regrowth after 24 hour reincubation. The triple combination of M-EDTA in 25% ethanol completely eradicated the organisms on the silicone disks after 1 hour exposure. Furthermore, the level of regrowth associated with a triple combination after 24 hours of reincubation was significantly lower than all the other alternative agents or their dual combination.

TABLE 5

Silicone Disk Bioprosthetic Colonization *Candida Parapsilosis* Model

| Drug Combinations Tested | 1 hour in Drug Mean CFU C. Parapsilosis | 24 h Growth after 1 hour in Drug Mean CFU C. Parapsilosis |
| --- | --- | --- |
| 3 mg/ml minocycline n = 5 | 5000.0 ± 0.0 | 5000.0 ± 0.0 |
| 30 mg/ml EDTA n = 5 | 5000.0 ± 0.0 | 5000.0 ± 0.0 |
| 25% EtOH in MHB n = 10 | 1933 ± 601.6 | 3875.0 ± 618.3 |
| 3 mg/ml minocycline/30 mg/ml EDTA n = 10 | 4080 ± 585.0 | 500.0 ± 0.0 |
| 25% EtOH/30 mg/ml EDTA n = 10 | 1666.7 ± 629.9 | 2333.0 ± 666.7 |
| 25% EtOH/3 mg/ml minocycline n = 10 | 1490.0 ± 542.4 | 5000.0 ± 0.0 |
| 25% EtOH/30 mg/ml EDTA/3 mg/ml minocycline n = 10 | 0 | 582.9 ± 264.5 |
| Control (MH Broth alone) n = 10 | 5000.0 ± 0.0 | 5000.0 ± 0.0 |

Thus, the two in vitro models of colonization (the modified Robbins device as well as the silicone disk bioprosthetic colonization model) show that the triple combination is uniquely and highly effective in eradicating organisms embedded in biofilm on latex and silicone polymers with minimal or no regrowth after 24 hour exposure to the combination. These two models are predictive of the clinical efficacy of this triple combination in eradicating organisms embedded in biofilm on catheters at a temperature of 37° C.

Hence, the triple combination is superior in efficacy to the combination of minocycline and EDTA, EDTA and ethanol or minocycline and ethanol.

All of the compositions and/or methods and/or apparati disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and/or apparati and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Provisional Patent Application Ser. No. 60/261,447
U.S. Provisional Patent Application Ser. No. 60/316,165
U.S. Non-Provisional patent application Ser. No. 10/044,842
U.S. Pat. No. 5,362,754
U.S. Pat. No. 5,688,516
U.S. Pat. No. 6,350,251
Bleyer et al., In: Proceedings of the 4th Decennial International Conference on Nosocomial and Healthcare-Associated Infections in conjunction with the 10th Annual Meeting of the Society for Healthcare Epidemiology of America, Atlanta, Ga., pp 91, 2000.
Carratala et al., *Antimicrob. Agents Chemother.*, 43:2200-2204, 1999.
Centers for Disease Control and Prevention, *MMWR*, 51 (RR-10), 2002.
Chatzinikolaou et al., *Clin. Infect. Dis.*, 36(1):116-9 (2003).
EP1245247
Evans et al., *Antimicrob. Agents Chemother.*, 31(6):889-894, 1987.
Henrickson et al., *J. Clin. Oncol.*, 18:1269-1278, 2002.
Kuhn et al., *Antimicrob. Agents Chemother.*, 46(6):1773-1780, 2002.
Kluger et al., In: Interscience Conference on Antimicrobial Agents and Chemotherapy (ICAAC) Abstracts of the 39$^{th}$ Meeting, 514, 1999.
Maki et al., In: Hospital Infections. Bennett J V, Brachman P S, eds. Lippincott-Raven, Philadelphia, Pa., pp 689-94, 1998.
Mermel et al., *Clin. Infect. Dis.* 32:1249-1272, 2001.
Nickel et al., *Dialogues in Pediatric Urology*, 14(10):7-8, 1991.
Raad et al., *J. Infect. Dis.* 168:400-407, 1993.
Raad et al., *Antimicrob. Agents Chemother.*, 46(2):327-332, 2002.
Raad et al., *Arch. Intern. Med.* 162:871-878, 2002.
Reardon et al., *Medical Laboratory Sciences*, 48:72-75, 1991.
Sherertz et al., In: Proceedings of the 12th Annual Meeting of the Society for Healthcare Epidemiology of America (abstract #52676), Salt Lake City, Utah, Apr. 7-9, 2002.
Schwartz et al., *J. Clin. Oncol.*, 8:1591-1597, 1990.
Spafford et al., *MMWR*, 44:1-13, 1994.

What is claimed is:

1. An antimicrobial solution comprising ethanol, EDTA and either minocycline or trimethoprim, wherein the concentration of ethanol is in the range of 10% to 45% (v/v), the ethanol, EDTA and minocycline or trimethoprim being present in amounts effective to eradicate *Candida parapsilosis* or methicillin resistant *S. aureas* embedded in a biofilm.

2. The solution of claim 1, wherein the concentration of the ethanol is in the range of 10-40%.

3. The solution of claim 2, wherein the concentration of ethanol is in the range of 15-30%.

4. The solution of claim 3, wherein the concentration of the ethanol is about 25%.

5. The solution of claim 1, comprising ethanol, minocycline and EDTA.

6. The antimicrobial solution of claim 1, wherein said solution is defined as comprising ethanol, trimethoprim or minocycline, Ca(II)-EDTA, and propylene glycol in a physiologically acceptable saline solution.

7. The antimicrobial solution of claim 1, wherein the solution comprises trimethoprim.

8. The antimicrobial solution of claim 7, further comprising propylene glycol.

9. A syringe, comprising a unit dose of a pharmacologically effective amount of a solution in accordance with any one of claims 1, 2-4, 5, 7 or 8.

10. A vial, comprising a unit dose of a pharmacologically effective amount of a solution in accordance with any one of claims 1, 2-4, 5 or 7-6.

11. A medical device locking solution comprising a solution in accordance with any one of claims 1, 2-4, 5 or 7.

* * * * *

UNITED STATES PATENT AND TRADEMARK OFFICE
CERTIFICATE OF CORRECTION

PATENT NO. : 7,601,731 B2
APPLICATION NO. : 10/862830
DATED : October 13, 2009
INVENTOR(S) : Issam Raad Page 1 of 1

It is certified that error appears in the above-identified patent and that said Letters Patent is hereby corrected as shown below:

In claim 9, column 24, line 35, delete "claims 1, 2-4, 5, 7 or 8" and insert --claims 1-8-- therefor.

In claim 10, column 24, line 38, delete "claims 1, 2-4, 5 or 7-6" and insert --claims 1-8-- therefor.

In claim 11, column 24, line 40, delete "claims 1, 2-4, 5 or 7" and insert --claims 1-8-- therefor.

Signed and Sealed this
Twenty-third Day of August, 2011

David J. Kappos
*Director of the United States Patent and Trademark Office*